(12) United States Patent
Donnet et al.

(10) Patent No.: US 9,211,131 B2
(45) Date of Patent: Dec. 15, 2015

(54) INSTRUMENT FOR TREATING BIOLOGICAL TISSUE, METHOD FOR GENERATING SHOCK WAVE-LIKE PRESSURE WAVES IN SUCH AN INSTRUMENT

(75) Inventors: Marcel Donnet, Saint de Gonville (FR); Mathieu Benoit, Jongny (CH); Kossi Agbeviade, Morrens (CH)

(73) Assignee: FERTON HOLDING S.A., Delemont (CH)

( * ) Notice: Subject to any disclaimer, the term of this patent is extended or adjusted under 35 U.S.C. 154(b) by 935 days.

(21) Appl. No.: 13/127,203

(22) PCT Filed: Oct. 30, 2009

(86) PCT No.: PCT/EP2009/064362
§ 371 (c)(1),
(2), (4) Date: Jun. 29, 2011

(87) PCT Pub. No.: WO2010/049519
PCT Pub. Date: May 6, 2010

(65) Prior Publication Data
US 2011/0275965 A1    Nov. 10, 2011

(30) Foreign Application Priority Data

Oct. 31, 2008 (EP) .................................... 08168076

(51) Int. Cl.
*A61B 17/225* (2006.01)
*A61B 17/22* (2006.01)
(Continued)

(52) U.S. Cl.
CPC ........ *A61B 17/22004* (2013.01); *A61H 23/008* (2013.01); *A61B 2017/0019* (2013.01);
(Continued)

(58) Field of Classification Search
CPC ..... A61H 23/00; A61H 23/04; A61H 23/004; A61H 23/008; A61B 17/22004; A61B 2017/00154; A61B 2017/0019; A61B 2017/00544; A61B 2017/924; A61B 2017/927
USPC ......... 601/2, 4, 46, 107–108; 606/1, 127–128
See application file for complete search history.

(56) References Cited

U.S. PATENT DOCUMENTS 3,250,334 A * 5/1966 Sussman ......................... 173/18
3,955,563 A    5/1976 Maione
(Continued)

FOREIGN PATENT DOCUMENTS

DE    20 2007 007 921 U1    11/2008
DE    202007007921 U1    11/2008
(Continued)

OTHER PUBLICATIONS

European Search Report dated Sep. 12, 2012, as issued in European Patent Application No. 12181915.5.
(Continued)

*Primary Examiner* — Justine Yu
*Assistant Examiner* — Timothy Stanis
(74) *Attorney, Agent, or Firm* — Maier & Maier, PLLC

(57) ABSTRACT

The invention relates to an instrument for treating biological tissue, including a housing, in which is disposed a ballistic device for generating extracorporeal shock wave-like pressure waves and a transfer element permanently placed on the biological tissue, said element coupling the pressure waves into the body of living creatures, wherein the transfer element couples non-focused, ballistically generated, shock wave-like pressure waves into the biological tissue, the waves generated by a striking member that is accelerated to a high final velocity of over 5 m/s by a pneumatic medium which is under an operating pressure in a pressure channel. A quick-acting valve releases the pneumatic medium, which is under working pressure, into the pressure channel, wherein a control circuit controls the duration of opening of the valve as a function of at least one or a combination of the following parameters: working pressure, impact frequency or pressure in the back-pressure chamber.

12 Claims, 3 Drawing Sheets

(51) Int. Cl.
  *A61H 23/00* (2006.01)
  *A61H 23/04* (2006.01)
  *A61B 17/00* (2006.01)
  *A61B 17/92* (2006.01)

(52) U.S. Cl.
  CPC .......... *A61B2017/00154* (2013.01); *A61B 2017/00544* (2013.01); *A61B 2017/924* (2013.01); *A61B 2017/927* (2013.01); *A61H 23/04* (2013.01)

(56) References Cited

U.S. PATENT DOCUMENTS

| | | | | |
|---|---|---|---|---|
| 4,549,535 | A | * | 10/1985 | Wing ............................ 601/108 |
| 4,716,890 | A | | 1/1988 | Bichel |
| 5,160,336 | A | | 11/1992 | Favre |
| 5,727,556 | A | * | 3/1998 | Weth et al. .................... 600/439 |
| 5,853,384 | A | | 12/1998 | Bair |
| 6,413,230 | B1 | | 7/2002 | Haupt et al. |
| 6,736,784 | B1 | * | 5/2004 | Menne et al. .................... 601/2 |
| 2002/0177795 | A1 | * | 11/2002 | Frye .............................. 601/84 |
| 2005/0209586 | A1 | * | 9/2005 | Menne et al. .................... 606/1 |
| 2006/0069395 | A1 | | 3/2006 | Lebet |
| 2010/0137760 | A1 | | 6/2010 | Schulz et al. |

FOREIGN PATENT DOCUMENTS

| | | |
|---|---|---|
| EP | 1574198 A1 | 9/2005 |
| EP | 1 574 198 B1 | 7/2007 |
| WO | 98/57707 A1 | 12/1998 |
| WO | 9857707 | 12/1998 |

OTHER PUBLICATIONS

International Search Report, dated Jan. 26, 2010 in corresponding International Patent Application No. PCT/EP2009/064362, 7 pages.

* cited by examiner

INSTRUMENT FOR TREATING BIOLOGICAL TISSUE, METHOD FOR GENERATING SHOCK WAVE-LIKE PRESSURE WAVES IN SUCH AN INSTRUMENT

RELATED APPLICATIONS

This application is the U.S. national stage application which claims priority under 35 U.S.C. §371 to International Patent Application No.: PCT/EP2009/064362 filed on Oct. 30, 2009, which claims the benefit of priority under 35 U.S.C. §119, to European Patent Application No.: 08168076.1, filed on Oct. 31, 2008, the disclosures of which are incorporated by reference herein their entireties.

The invention refers to an instrument for the treatment of biological tissue and to a method for generating shock wave-like pressure waves in such an instrument.

Such instruments are known from WO9857707 and serve to accelerate the healing process of bone fractures, enthesiopathies, tendopathies, but also in cases of periodontitis, using shock wave-like non-focused pressure waves. Another field of application is pain therapy in the soft tissue regions of the musculoskeletal system near bones.

Other known pressure pulse sources serving the same therapeutic purposes use focused shock waves and can be effective only in the very limited focal region. For a satisfactory therapy result, however, the entire region of a bone fracture has to be treated uniformly with sound waves. This requires a complex moving mechanism for the pressure pulse source and a positioning system to be able to set the focus onto the treatment site. The positioning systems that are used during the treatment to localize the treatment site (ultrasound and x-ray) are unable to concretely indicate the source of pain and the attending doctor irradiates the presumed source of pain with a large number of single pulses. However, such an approach is very time-consuming because the treatment positions have to be retrieved repeatedly.

The generic instrument for the treatment of biological tissue of a human or an animal body, known from WO9857707, comprises a shock wave generator generating non-focused shock waves or shock wave-like pressure waves that, in a simple and cost-effective manner, allow for a uniform energy distribution of the pressure waves over a large-surface effective area. To achieve this, a housing is provided with a ballistic means for generating extracorporeal shock wave-like pressure waves and a transfer element that is permanently placed on the biological tissue during operation and couples the pressure waves into the body of living beings. The transfer element couples non-focused ballistically generated shock wave-like pressure waves into the biological tissue. The pressure waves are generated by a reciprocating striking member accelerated to a high final velocity and striking on the transfer element. The striking member is accelerated to a velocity of more than 5 m/s by a pneumatic medium under working pressure. The front part of the pressure channel is connected to a back-pressure chamber into which the pneumatic medium located distally in front of the striking member can flow as the striking member is accelerated towards the transfer element.

The ballistic means for generating shock wave-like pressure waves comprises a striking member guided in a housing and adapted to be reciprocated by means of a pneumatic drive means, wherein the striking member exerts one or a plurality of impulses on the transfer element and, due to the impulses, induces shock wave-like pressure waves into the almost immobile transfer element, which propagate to the tip of the transfer element. The pressure waves with their high pressure peak values are thus generated ballistically in a simple manner. When compared with pressure wave generators using focused shock waves, the pressure waves obtained with a system as above reach similar characteristic values with respect to rise time, maximum pressure peak and energy flow density. The non-focused pressure wave propagates radially in the biological tissue to the application site.

Essential advantages of the instrument are that the instrument has a simple, low-cost structure whose manufacturing costs are low compared to known pressure wave generators for focused shock waves. The medical instrument is realized as a small portable device that is easier to apply and can be placed on the body portion to be treated without any encumbrance. The device requires no consumables and in particular no positioning devices, since the treatment region is close to the probe tip.

It is a purpose of the known instrument not to focus the shock wave-like pressure waves and to thereby allow these to be coupled in over a large surface.

Thus, a positioning system can be omitted. The instrument is particularly suitable for treatments where the probe tip can be placed on the body surface very closely to the application site, as it is the case, for instance, with tennis elbows, calcaneal spurs or also with diseases of the skin.

It is an object of the invention to develop the instrument mentioned above and a method for generating shock wave-like pressure waves such that it is possible to couple in a higher pressure wave energy without enlarging the instrument and without increasing the working pressure, and to increase the striking frequency.

The invention advantageously provides that a quick-action valve releases the pneumatic medium under working pressure, wherein a control circuit controls the opening time of the valve as a function of one or a combination of the following parameters, i.e. the parameters of working pressure, striking frequency or pressure in the back-pressure chamber.

Using a control circuit for a quick-action valve, the invention makes it possible to increase the energy of the shock wave-like pressure waves that can be coupled in, and thus to increase the pressure peak values of the pressure waves, without enlarging the dimensions of the instrument or to significantly increase the pneumatic working pressure for the ballistic means. Another advantage is the increase in the striking frequency of the individual impact pulses caused by the striking member, so that the treatment time can be shortened. A shortening of treatment time is more pleasant to the patient. The control circuit controls the opening time of the valve as a function of the working pressure applied or a preset striking frequency or the pressure in the back-pressure chamber, so that the pressure build-up and the use of the available working pressure in accelerating and returning the striking member can be optimized. The pneumatic energy available can be used with 40% more efficiency. Another advantage of such a control is the possibility of setting the strength of each individual striking impulse such that it only depends on the working pressure selected and does not change even for different striking frequencies. In other words: the control of the present invention guarantees that the striking intensity is constant for high striking frequencies.

Controlling the opening period and the opening and closing times is advantageous in particular at high striking frequencies in order to make efficient use of the prevailing working pressure and to optimally accelerate the striking member with the existing pneumatic energy.

As an alternative it may be provided that a quick-acting valve releases the pneumatic medium under working pressure in dependence on the striking frequency set, an opening in the back-pressure chamber limiting the pressure building up in the back-pressure chamber. The opening has a small diameter compared to the volume of the back-pressure chamber, so that not all of the pressurized air in the back-pressure chamber can escape at once, but a certain back-pressure is maintained for a certain time.

The opening in the back-pressure chamber connects the back-pressure chamber either with atmosphere or with a further chamber that may also be configured as a pressure storage. In this context, an embodiment is particularly preferred in which the chamber is a pressure storage with elastic walls. Here, the opening in the back-pressure chamber forms a sort of throttle.

The opening in the back-pressure chamber, which connects to atmosphere, may be formed by a narrow orifice or a valve, in particular a pressure relief valve.

Accordingly, the object may also be achieved if the pressure in the back-pressure chamber is changed during pressure build-up. Since the pressure building in the back-pressure chamber can interfere with an optimal acceleration of the striking element, an optimization is also possible if the magnitude of the back-pressure can be limited or controlled.

The pressure in the back-pressure chamber may be controlled by means of an adjustable or controllable or drivable pressure relief valve.

With a controllable valve, the pressure in the back-pressure chamber can be controlled in dependence on at least one of or a combination of the following parameters, namely the parameters of working pressure, striking frequency and pressure in the back-pressure chamber.

Using such a pressure relief valve can prevent the occurrence of too high a back-pressure in the back-pressure chamber. The pressure relief valve may be adjustable to a defined limit value or it may be variably controllable in dependence on predetermined parameters.

The quick-action valve is preferably integrated in the housing. Arranging the quick-acting valve in the housing allows for short connecting paths to the pressure channel or the back-pressure chamber.

The short connecting paths guarantee for a fast pressure build-up, in particular in the pressure channel, so that an energy-efficient use of the prevailing working pressure is possible.

In a preferred embodiment, the quick-action valve releases the pneumatic medium from an intermediate storage integrated in the housing, the storage buffering the medium at a predetermined working pressure. The intermediate storage is connected to the supply pressure of a pressure source, the pressure in the intermediate buffer being set to a pre-settable or controllable working pressure.

The intermediate storage is preferably arranged near the valve.

Similarly, the arrangement of the intermediate storage near the valve also results in short connecting paths with little pressure loss so that the pneumatic medium present at working pressure in the intermediate storage can be introduced into the pressure channel with practically no pressure loss. Due to the short connecting paths, pressure can build up faster in the pressure channel.

The intermediate storage may be arranged near the pressure channel and may be pneumatically connected to the pressure channel via the valve and through a connecting conduit that is shorter than the length of the pressure channel or short with respect to the length of the pressure channel.

As an alternative to the arrangement within the housing of the instrument, the intermediate storage may also be arranged in the pneumatic medium supply conduit that connects the housing or valve with the pneumatic drive means (pressure source). In this context, the pneumatic drive means preferably is a compressor with a pressure storage.

The valve has switching times of less than 5 ms, preferably less than 3 ms. Short switching times of the valve are necessary to obtain high striking frequencies. Switching times of 1 ms and less are preferred.

In an alternative embodiment, it may be provided to pressurize the back-pressure chamber for the return movement of the striking member.

It may also be provided that a second valve releases a pneumatic pressure into the back-pressure chamber to cause the return movement of the striking member.

According to another embodiment, a respective intermediate storage may be provided for the pressure channel and for the back-pressure chamber.

Preferably, it is provided that a single valve controls the forward and the return movement of the striking member.

The volume of the at least one intermediate storage is preferably at least half the volume of the pressure channel or at least half the volume of the pneumatic means needed in a stroke of the striking member. The volume of the intermediate storage is thus adapted to the volume necessary for the acceleration of the striking member. Tests have shown that a high working pressure available in the first half of the acceleration phase already results in significantly higher final velocities of the striking member. When the intermediate storage is further enlarged, the final velocity of the striking member only increases slightly. It is essential that the pressure medium in the intermediate storage can be connected with the pressure channel via a short path, so that the pressure build-up can occur quickly enough. Since the intermediate storage is connected with a pressure vessel of the pneumatic drive means, which is at working pressure, it is guaranteed that the intermediate storage is refilled quickly enough, so that the working pressure in the pressure channel can be maintained until the closing signal for the control of the valve.

In another embodiment, a change-over valve can alternately supply working pressure from the at least one intermediate storage to the pressure channel or the back-pressure chamber.

Further, a change-over valve may also alternately open the pressure channel or the back-pressure chamber to atmosphere.

In this case, the working pressure may be relieved from pressure channel after acceleration of the striking member and the back-pressure chamber may also be relieved from pressure after the striking member has returned to its home position.

In an alternative embodiment a change-over valve may alternately supply pressure to the pressure channel or the counter-pressure channel.

Here, a pressure storage and a vacuum storage may be provided, a change-over valve alternately connecting the storages with the pressure channel or the back-pressure chamber.

The at least one pressure storage of all embodiments may have elastic walls. In this case, the pressure storage resembles a sort of balloon. Thereby, the back-pressure in the back-pressure chamber is slightly dependent on the position of the striking member along the pressure channel. In any case, the pressure increase in the back-pressure chamber is less steep if elastic walls are provided. An elastic wall in a pressure storage could also be formed by a piston in a piston/cylinder unit, which works against a spring.

In a method for controlling a striking member in an instrument for the treatment of biological tissue, it is possible either to control the opening period of a quick-action valve as a function of at least one parameter or a combination of the following parameters, i.e. the working pressure or the striking frequency or the pressure in the back-pressure chamber, or to limit the pressure building up in the back-pressure chamber. This may also be done in dependence on at least one or a combination of the following parameters, namely the parameters of working pressure, striking frequency and pressure in the back-pressure chamber. Controlling the quick-action valve with respect to opening times and/or opening periods may also be provided in the latter alternative.

It is advantageous especially in orthopedic applications to couple a plurality of pressure waves into the biologic tissue so as to achieve an optimal effect. Therefore the ballistic means is preferably configured such that a periodic reciprocating movement of the striking member is possible. The striking frequency is up to 50 Hz, preferably up to 60 Hz.

Between the probe tip and the coupling site on the biological tissue, an impedance adjustment medium can be provided that enhances the coupling of the pressure wave into the biological tissue. A suitable pasty impedance adjustment medium is an ultrasound gel, for instance, or another pasty mass such as petrolatum.

The length of the transfer element may range from about 20 to 100 mm. An adaptation to a desired treatment can be achieved by means of different and exchangeable transfer elements.

The following is a detailed description of the invention with reference to the drawings.

Figure 1:
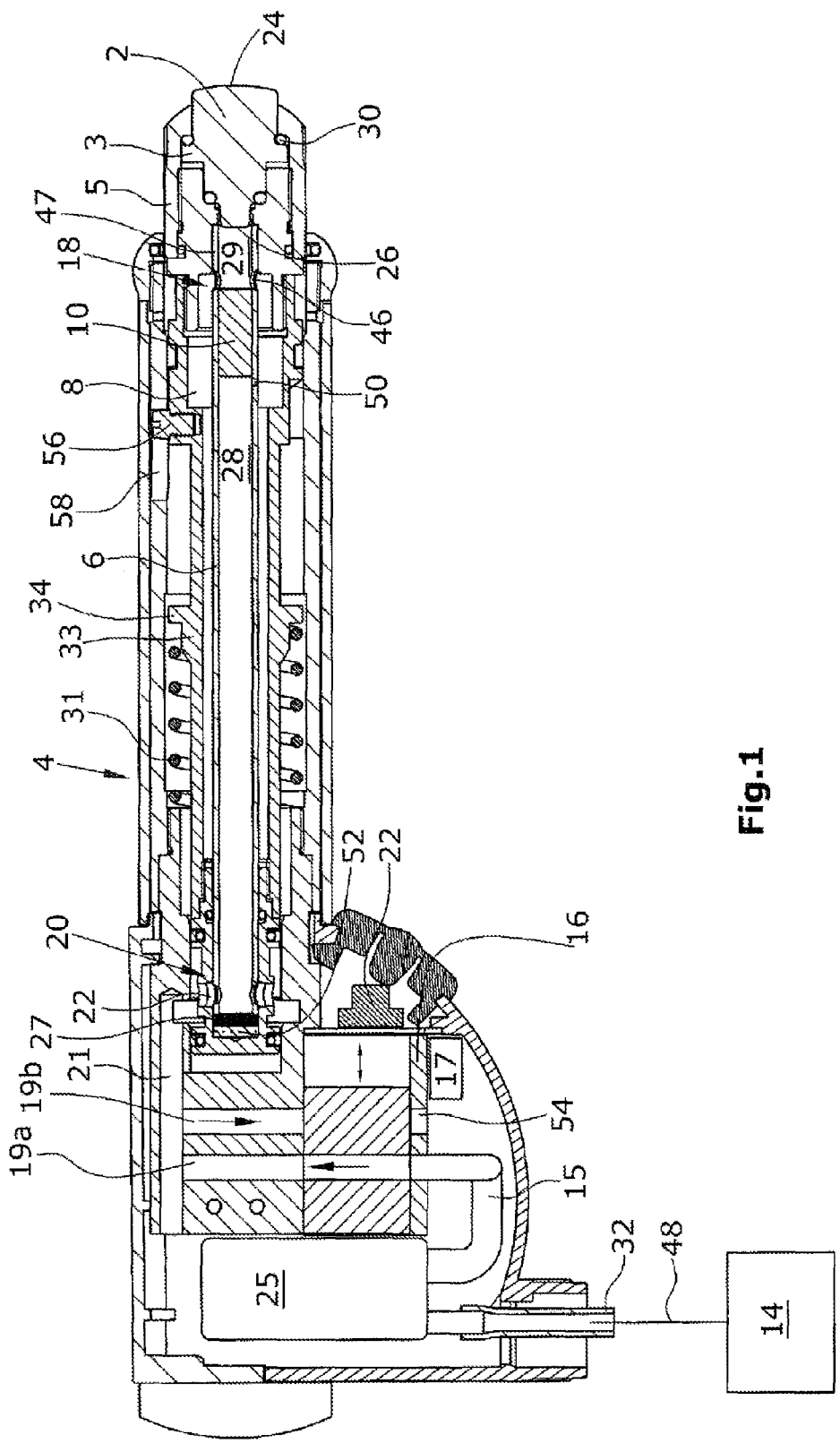
FIG. 1 is a cross section of the instrument.

The medical instrument allows the treatment of biological hard and soft tissue, in particular for healing bone ailments such as bone fractures, enthesiopathies, tendopathies, but also in cases of periodontitis, as well as for pain therapy in the soft tissue regions of the musculoskeletal system near bones, by coupling ballistically generated, non-focused pressure waves into the biological tissue via a transfer element 2 that is blunt at the body contact surface.

The hand-held device is formed by a housing 4 accommodating a pressure channel 6 in which a striking member 10 is reciprocated between two end positions by means of pneumatic driving means 14 in combination with a back-pressure chamber 8 that surrounds the pressure channel 6 in a coaxial annular manner, for instance. For a pneumatic drive, the acceleration path is about 100 to 250 mm in length.

In the proximal end position of the striking member 10, a magnetic holder and/or a, possibly elastic, stop element 27 may be provided at the proximal end 20 of the pressure channel 6. A magnetic holder can retain the metal striking member 10 at its proximal end position until a valve again releases pneumatic pressure applied via the connection 32, and accelerates the striking member 10 towards the distal end 18 of the pressure channel 6. The air located in front of the striking member 10, seen in the direction of movement of the striking member 10, is introduced into the back-pressure chamber 8 via openings 46 at the distal end 18 of the pressure channel 6.

Due to the acceleration of the striking member 10 the same strikes on an end face 26 of the transfer element 2, situated distally in front of the pressure channel 6, with a high ballistic final velocity of more than 5 m/s, for example. The transfer element 2 has a planar or curved contact surface 24. The striking member 10 exerts one or a plurality of impulses on the transfer element 2 which transmits the pressure waves induced into the transfer element 2 by the striking member 10 to the contact surface 24, where they are coupled into a biological tissue.

The transfer element 2 is guided linearly in the housing 4, and preferably coaxially to the striking member 10. The housing 4 has a head part 5 that can be unthreaded to change the transfer element 2. The transfer element 2 is supported in a bore of the head part 5 and may be sealed by means of a non-illustrated O-ring seal at the front portion of the head part 5. An annular bead 3 of the transfer element 2 serves as a stop element, with a spring/damper element 30 being arranged between the annular bead 3 of the transfer element 2 and the head part 5 of the housing 4, which spring/damper element decouples the transfer element 2 from the housing 4 in the axial direction. For a coupling of the pressure wave into the biological tissue, shifting the transfer element 2 is not necessary and mostly unwanted so as to avoid injuries.

When the pressure present at the pneumatic connection 32 disappears, the back-pressure building up in the back-pressure chamber 8 is sufficient to return the striking member 10 from the distal end position at the transfer element 2 to the proximal end position. The pneumatically controllable pressure at the connection 32 may be up to 6 bar, for instance, preferably 4 bar. In order to adapt to certain lengths of the transfer element 2 or to generate a certain characteristic of the pressure wave, the striking member 10 may be chosen with different lengths, masses and maximum impact velocity, and they are easily changed by unthreading the head part 5. Typical maximum pressure values at the tip of the transfer element 2 are between 2 and 25 MPa with rise times of 0.5 to 3 µs and energy flow densities between 0.05 and 0.6 mJ/mm$^2$.

The proximal end face 26 of the transfer element 2 may have about the same diameter as the striking member 10. The length of the striking member 10 is preferably larger than its diameter. Thereby, better guiding characteristics are achieved in the pressure channel 6. Moreover, the use of different lengths makes it possible to vary the mass of the striking member 10 in a rather simple manner without having to modify the diameter of the pressure channel 6 and the inlet boundary surface 26 of the transfer element 2.

For the generation of a pneumatic acceleration pulse quickly opening and closing valves are suitable that are arranged in the supply line. Since the acceleration process temporarily requires larger volumes of air, it is advantageous to provide an intermediate storage 25 in the supply line 48 that is ideally arranged in the housing 4 and near the valve 16.

For a faster opening or switching of the valve 16, an electric or electronic control circuit 17 is used. In such a control circuit 17, particularly high currents can be provided in the opening phase, which are later lowered to normal level. Switching times of less than 1 ms can be achieved with such electrically controllable valves 16. In general, the switching times of the valve 16 should be below 5 ms, preferably below 3 ms. The opening period of the valve is between 3 and 35 ms, for instance, depending on the working pressure and the striking frequency.

It is advantageous in order to reduce the required volumes of pneumatic medium, preferably air, to keep the volume necessary for an individual pressure pulse as small as possible.

An electric pressure switch 22 is connected to the control circuit 17 that controls the electrically or electronically controllable valve 16. Therefore, the valve 16 is integrated in the housing 4 of the instrument.

The instrument for the treatment of biological tissue is not meant for the generation of only single pressure pulses, since medical indications rather require a larger number of pressure pulses. Typical values are in the range between 1000 and 5000 pulses, in certain special cases the number is significantly higher. Therefore, the instrument is intended to be able to provide this number of pulses in a short time to avoid any unnecessary protraction of the treatment time.

In this context, the volume of the back-pressure chamber 8 should be set such that a back-pressure is built up that is sufficiently high to return the striking member 10. The higher the back-pressure is, the faster the striking member 10 is returned. However, too high a back-pressure strongly decelerates the forward movement of the striking member 10 and thus reduces its impact effect on the transfer element 2.

Further, it has been found that not only the air volume present in front of the striking member 10 builds up the back-pressure in the back-pressure chamber 8, but that in addition, due to the working pressure behind the striking member 10, a leakage volume flows past the striking member 10 into the back-pressure chamber 8 and influences the mean pressure prevailing there. Thereby, the parameters for returning the striking member 10 are changed and, along with this change, the predefined performance values of the apparatus will change with the progress in treatment time. This can be counteracted by additional means for adjusting the pressure in the back-pressure chamber 8.

The pressure in the back-pressure chamber 8 can be limited, for example, connecting the back-pressure chamber 8 to atmosphere by means of a throttle-like opening 61 in the back-pressure chamber 8 and by means of small openings 62.

Figure 2:
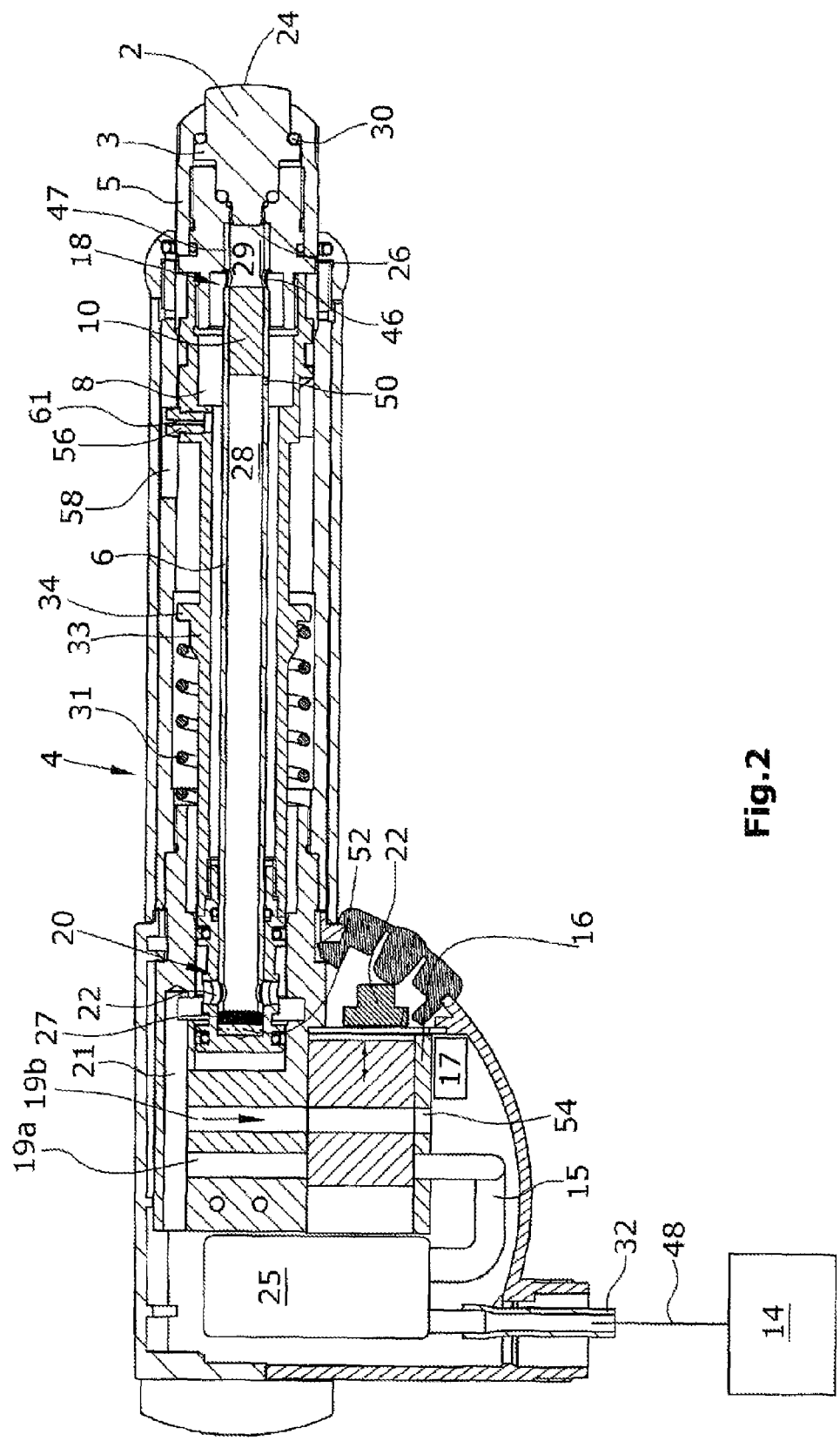
FIG. 2 illustrates the instrument of FIG. 1 in another switching position of the valve.
Figure 3:
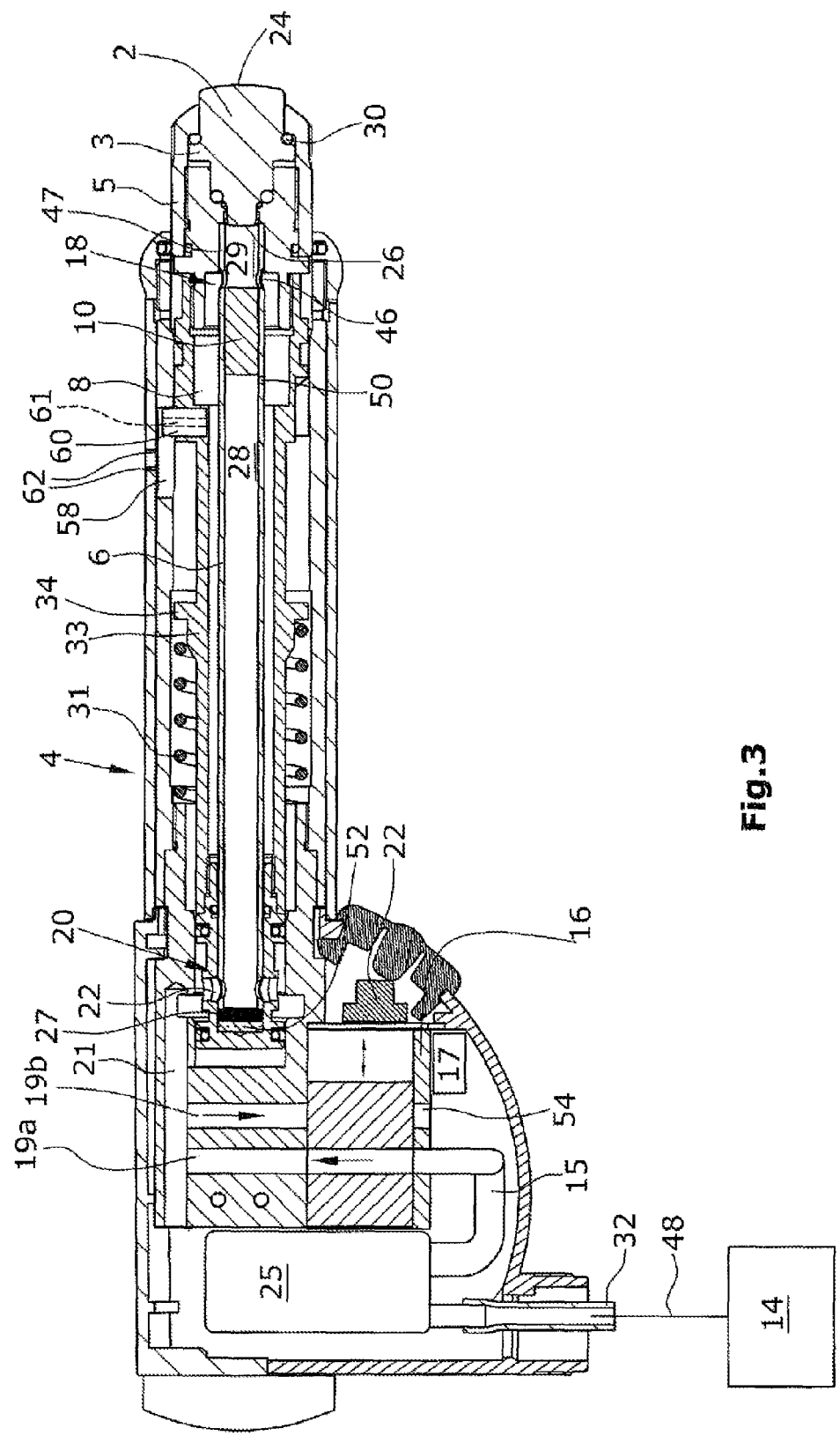
FIG. 3 illustrates a second embodiment of the instrument.

The opening 61 in the back-pressure chamber 8 may be provided, for example, in the screw 56 shown in FIG. 2 or in the valve 60 as illustrated in FIG. 3.

Through these openings 61, 62 to atmosphere, the pneumatic medium can flow out and thus reduce the back-pressure in the back-pressure chamber 8. If the pressure in the back-pressure chamber 8 is particularly high, a larger air volume also flows through the openings 61, 62.

As an alternative, a valve 60 may be provided which opens or closes an opening 61 to atmosphere. This may be a pressure limiting valve or a controllable valve that opens and closes, in combination with a pressure meter, in dependence on a predefined back-pressure in de back-pressure chamber 8.

As an alternative, a pressure relief valve may be provided that opens automatically when a value to be set is exceeded.

If a higher pressure is needed in the back-pressure chamber 8, the back-pressure chamber 8 can also be connected to a pressure storage via a switchable valve 60, wherein a connection can be made to the intermediate storage 25 or to a separate pressure storage for the back-pressure chamber 8.

The screw 56 threaded into the sleeve 33 near the distal end of the housing 4 serves as a anti-rotation means and a stop means for limiting the stroke of the spring 31. The screw 56 is guided in a groove 58 of the housing 4. The screw may also be provided with the opening 61.

Instead of the screw 56, it is also possible to provide a valve 60 with an opening 61 at this position, which connects the back-pressure chamber 8 to atmosphere. As can be seen in FIG. 3, the back-pressure chamber 8 may be connected to atmosphere via the valve 60, e.g. a pressure relief valve, so that the maximum pressure in the back-pressure chamber 8 can be controlled. In this case, the outer wall of the housing 4 has openings 62 to atmosphere provided in the region of the groove 58.

A connection of the back-pressure chamber 8 to atmosphere via an opening 61 or via a valve 60 for limiting the pressure building up in the back-pressure chamber 8 is applicable both when the quick-action valve is controlled with respect to its opening period and when the valve is controlled only with reference to the striking frequency and the valve opening period is constant.

A limitation or control of the pressure in the back-pressure chamber 8 may also be effected in combination with a quick-action valve 16 using variable control times and a variable opening period of the valve.

In the simplest embodiment, the back-pressure chamber 8 merely has a narrow opening 61 in the manner of a throttle site connecting the back-pressure chamber 8 either to atmosphere or to a further chamber, e.g. to the annular chamber located below the groove 58, in which the sleeve 33 is arranged. The opening in the manner of a throttle site allows the back-pressure in the back-pressure chamber to drop, especially when high pressures prevail.

If the opening leads to a further chamber, the same is preferably designed as an elastic pressure storage, e.g. in the manner a balloon or in the manner of a piston/cylinder unit, in which the piston can be displaced against the force of a spring.

For a control of the movement of the striking member 10, it is also possible to control the control times of the valve 16 and the opening period of the valve 16. The striking member 10 is returned to its home position not only by the back-pressure in the back-pressure chamber 8, but the impact on the transfer element 2 imparts further kinetic energy to the striking member 10 that thrusts the striking member 10 back towards its home position. Given a corresponding design of the boundary wall 27 at the proximal end 20 of the pressure channel 6, the elastic rear boundary wall 27 may also produce an elastic thrust when colliding with the striking member 10, so that a part of the kinetic energy of the rebound can also be used for the forward movement of the striking member 10. To achieve this, it is feasible to actively influence the movement of the striking member. This may be done, for instance, by setting the control times of the valve 16 variably.

The control circuit 17 is adapted to control the opening period of the valve 16 as a function of at least one or a combination of the following parameters, i.e. the parameters of working pressure, striking frequency or pressure in the back-pressure chamber 8. Moreover, the opening and closing times of the valve 16 can be controlled. Alternatively or additionally, the control circuit 17 is adapted to control maximum pressure in the back-pressure chamber 8 as a function of at least one or a combination of the following parameters, i.e. the parameters of working pressure, striking frequency or pressure in the back-pressure chamber 8. By controlling the opening time and the opening period of the valve 16, the striking member 10 can be optimized with respect to its reciprocating movement such that, given a comparable working pressure, the striking intensity can be increased by up to 40%, and it is further possible to increase the striking frequency. The improvement in striking intensity and striking frequency is achieved without any enlargement of the device and without any increase in working pressure, in any case without a significant increase.

For monitoring and controlling the switching points of the valve 16, measuring means may also be provided that detect the position or the movement of the striking member 10 and thus supply further information for controlling the switching times to the control circuit 17. For example, the pressure in the back-pressure chamber 8 can be measured, as well as reaching a certain position of the striking member 10 in the pressure channel can be detected, using optical measuring methods, for instance.

This means that the detection signal which indicates that the striking member 10 has reached a predetermined position in the pressure channel 6 can be used in controlling the valve 16. Thus, for example, the application of pressure to the pressure channel 6 may be terminated already before the striking member 10 hits the transfer element 2.

Further, the back-pressure in the back-pressure chamber 8 can be limited to a value that guarantees for a sufficiently fast returning of the striking member 10 to the proximal end position.

It is feasible for a repeated striking that the striking member 10 is self-returning. Several possible solutions exist to the problem of returning the striking member 10. Thus, returning the striking member 10 can also be effected using a controlled pneumatic pulse. A second valve can fulfill this task. To save costs, only a single valve 16 could be used that is adapted to alternately provide a pressurized air pulse for acceleration and for returning, respectively.

A kind of pneumatic spring has proven itself in practice. Here, the air space in front of the striking member and a back-pressure 8 in communication therewith form a closed region that is reduced by the forward directed movement of the striking member. Thereby, the pressure in this counter pressure chamber 8 is increased, whereby the striking member 10 can be returned to its home position after the accelerating compressed air pulse has been switched off. The volume of this back-pressure chamber 8 should be chosen such that, on the one hand, the forward movement of the striking member 10 is not hindered too much by the back-pressure building up and that, on the other hand, the back-pressure built up is sufficiently high to return the striking member 10 to its proximal home position fast enough.

If the striking member 10 is located motionlessly near the transfer element 2, for from its home position, it cannot be returned to a functional state at the proximal end 20 without any auxiliary means. A compressed air pulse would be useless. In order to return the apparatus to a functional state even in such situations, a small connecting opening between the back-pressure chamber 8 and the rear part of the pressure channel 6 may be provided. As a result, air can flow into the back-pressure chamber 8 so that the pressure therein will rise. Thereby, the striking member 10 can be returned to its initial proximal home position.

The instrument illustrated in FIG. 1 is supplied by a pneumatic drive means 14, preferably a compressor with a pressure vessel, with a supply pressure via the conduit 48 and the connection 32. The supply pressure is used to bring an intermediate storage 25 in the housing 4 to a pre-settable working pressure, for instance, 3 or 4 bar.

However, it is preferred that the supply pressure of the pressure vessel of the pneumatic drive means 14 already is at the working pressure, so that the intermediate storage 25 in the housing 4 can always be quickly refilled with pneumatic medium under the chosen working pressure, even as the intermediate storage 25 is emptied.

The pneumatic medium, preferably air, is supplied to the pressure channel 6 via the conduit 15 and a quick-acting, preferably electromagnetically controlled valve 16, as well as via the conduit 19a and the conduit 21, as well as the openings 22 uniformly distributed over the circumference of the pressure channel 6, whereby the striking member 10 can be accelerated from a home position at the proximal end 20 of the pressure channel 6 to a distal position. At the distal end 18 of the pressure channel 6, the striking member 10 hits the rear end face 26 of the transfer element 2 in a bullet-like manner and at a high velocity. Since the transfer element 2 is substantially at rest, the impact energy is transformed into a shock wave-like pressure wave which is coupled into the body at the distal front face 24 of the transfer element 2. The air which, due to the working pressure, expands in the space 28 behind the striking member 10 causes a compression of the air in the space 29 in front of the striking member 10, which air is introduced via openings 46, which are distributed over the circumference of the pressure channel 6, into a back-pressure chamber 8 preferably surrounding the pressure channel 6 in an annular cylindrical manner. The distal end of the pressure channel 6 may have slots 47 in the region distally in front of the openings 46, so that the air in front of the striking member 10 can still escape through the openings 46 into the back-pressure chamber 8. As can be seen in from the Figures, a connecting opening 50 between the pressure channel 6 and the back-pressure chamber 8 may be provided near the distal end 18 behind the striking member 10 in the position illustrated, which opening serves to also introduce the pressure prevailing in the space 28 into the back-pressure chamber 8 as soon as the striking member 10 has passed the connecting opening 50. Thus, a certain pressure equalization can be achieved between the two chambers, wherein the speed of the pressure equalization can be controlled by the diameter of the connecting opening 50.

It is essential that sufficient pressure prevails in the back-pressure chamber 8 after the striking member 10 has hit the transfer element 2, which pressure allows returning the striking member 10 in its proximal position. In this context, it is also important that, after the impact on the transfer element 2, a part of the kinetic energy of the striking member 10 is maintained by the elastic rebound from the transfer element 2, so that the pressure prevailing in the back-pressure chamber 8 can act to return the striking member 10.

Also at the proximal end 20 of the pressure channel 6, provisions have been made so that, in order to accelerate the striking member 10, the working pressure can get behind the striking member 10 when a series of striking pulses is first triggered. When a plurality of pulse series is executed, the rear boundary wall 27 of the pressure channel 6 may have elastic properties so that the striking member 10 can bounce back from the boundary wall 27 in the manner of an elastic impact. A magnet 52 may be arranged behind the boundary wall 27, which can retain the striking member 10 in the proximal end position when the pulse series are ended.

The transfer element with the head part 5, the pressure channel 6 and a sleeve 33 delimiting the back-pressure chamber 8 to the outside, can be moved in the proximal direction against the action of a compression spring 31, so that the transfer element can always be pressed against the biological tissue with a defined maximum contact pressure. On the one hand, the compression spring 31 abuts on a bead 34 of the sleeve 33 and, on the other hand, it abuts on the housing 4. Thus, the compression spring 31 prevents an excessive contact pressure of the transfer element 2 exerted on the biological tissue by an operator, e.g. via the end cap.

When the switch 22 is actuated, the electronic control circuit 17 causes the displacement of the valve 16 into the position illustrated in FIG. 1, so that the working pressure can flow from the intermediate storage 25 into the space 28 in the pressure channel 6. Thereafter, the control circuit 17 can control the opening period of the valve 16 as a function of the working pressure applied, the striking frequency set or the pressure in the back-pressure chamber 8, and it may in particular also determine the opening and closing times in the event of pulse series. In this manner, the pneumatic energy can be used more efficiently. In dependence on the above parameters, the control circuit 17 may also account for time delays due to inertia effects so that the switching times are always controlled in an optimum manner in terms of a more efficient utilization of energy.

In the closed position of the valve 16, as illustrated in FIG. 2, the connection between the connecting conduit 15 and the channel 19a is closed, while the connection between the channel 19b and the outlet 54 of the valve 16 is open, which channel may be connected to atmosphere for the relief of pressure from the pressure channel 6.

The invention claimed is:

1. An instrument for the treatment of biological tissue, comprising a housing in which are arranged a ballistic generator for generating extracorporeal shock wave pressure waves and a transfer element permanently placed on the biological tissue for coupling said pressure waves into the bodies of living beings, said transfer element coupling non-focused, ballistically generated, shock wave pressure waves into said biological tissue, which are generated by a reciprocating striking member accelerated to a final velocity of more than 5 meters/second by means of a pneumatic medium under working pressure in a pressure channel and striking said transfer element, a distal end of said pressure channel at which the transfer element is arranged being connected with a back-pressure chamber into which the pneumatic medium present distally of the striking member can flow as the striking member is accelerated towards the transfer element, wherein a quick-action valve releases the pneumatic medium under working pressure into the pressure channel, wherein a control circuit controls the opening period of the valve as a function of at least one or a combination of the parameters of working pressure, or pressure in the back-pressure chamber, resulting in the valve opening and/or closing as a function of at least one of the parameters of working pressure or pressure in the back-pressure chamber.

2. The instrument of claim 1, wherein the pressure in the back-pressure chamber is controlled by a controllable pressure relief valve as a function of at least one of the following parameters, striking frequency or pressure in the back-pressure chamber.

3. The instrument of claim 1, wherein said quick-action valve releases said pneumatic medium from an intermediate storage integrated in the housing, which buffers the medium at a predefined working pressure.

4. The instrument of claim 3, wherein the intermediate storage comprises elastic walls or at least one elastic wall.

5. The instrument of claim 1, wherein intermediate buffer is arranged near the pressure channel and is pneumatically connected to the pressure channel via said valve through a connecting conduit which is shorter than the length of the pressure channel or short.

6. The instrument of claim 1, wherein in a supply conduit for the pneumatic medium an intermediate storage is arranged.

7. The instrument of claim 1, wherein a second valve releases a pneumatic pressure into the back-pressure chamber for the return movement of the striking member.

8. The instrument of claim 1, wherein the volume of an intermediate storage is at least half the volume of the pressure channel volume or at least half the volume of the pneumatic medium required in one stroke of the striking member.

9. An instrument for the treatment of biological tissue, comprising a housing in which are arranged a ballistic generator for generating extracorporeal shock wave pressure waves and a transfer element permanently placed on the biological tissue for coupling said pressure waves into the bodies of living beings, said transfer element coupling non-focused, ballistically generated, shock wave pressure waves into said biological tissue, which are generated by a reciprocating striking member accelerated to a final velocity of more than 5 meters/second by means of a pneumatic medium under working pressure in a pressure channel and striking said transfer element, a distal end of said pressure channel at which the transfer element is arranged being connected with a back-pressure chamber into which the pneumatic medium present distally of the striking member can flow as the striking member is accelerated towards the transfer element, wherein a quick-action valve releases the pneumatic medium under working pressure into the pressure channel in dependence on the striking frequency set, wherein an opening in the back-pressure chamber limits the pressure building up in the back-pressure chamber, wherein said opening of the back-pressure chamber is formed by a narrow orifice or by a pressure relief valve.

10. A method for generating shock wave pressure waves pressure waves in an instrument for the treatment of biological tissue, wherein a ballistic means generates extracorporeal shock wave pressure waves and a transfer element permanently placed on the biological tissue couples said pressure waves into the bodies of living beings, wherein non-focused, ballistically generated, shock wave pressure waves are coupled into said biological tissue, which are generated by a reciprocating striking member accelerated to a final velocity of more than 5 meters/second by means of a pneumatic medium under working pressure in a pressure channel and striking said transfer element, a distal end of said pressure channel at which the transfer element is arranged being connected with a back-pressure chamber into which the pneumatic medium present distally of the striking member is introduced during the stroke movement of the striking member towards the transfer element, characterized by controlling the opening period of a quick-acting valve, releasing the working pressure into the pressure channel, as a function of at least one or a combination of the parameters of working pressure or pressure in the back-pressure chamber.

11. The method of claim 10 wherein limiting the maximum pressure in the back-pressure chamber as a function of one or a combination of the parameters of working pressure, striking frequency, or pressure in the back-pressure chamber.

12. A method for generating shock wave pressure waves in an instrument for the treatment of biological tissue, wherein a ballistic means generates extracorporeal shock wave pressure waves and a transfer element permanently placed on the biological tissue couples said pressure waves into the bodies of living beings, wherein non-focused, ballistically generated, shock wave pressure waves are coupled into said biological tissue, which are generated by a reciprocating striking member accelerated to a final velocity of more than 5 meters/second by means of a pneumatic medium under working pressure in a pressure channel and striking said transfer element, a distal end of said pressure channel at which the transfer element is arranged being connected with a back-pressure chamber into which the pneumatic medium present distally of the striking member is introduced during the stroke movement of the striking member towards the transfer element, characterized by introducing the working pressure into the pressure channel by means of a quick-acting valve in dependence on an adjustable striking frequency and limiting the pressure in the back-pressure chamber by partly venting the back-pressure chamber as the pressure builds up wherein the venting is made by using an opening in the back-pressure chamber, wherein said opening of the back pressure chamber is formed by a narrow orifice or by a pressure relief valve.

* * * * *